United States Patent [19]

Bunker

[11] Patent Number: 4,552,896
[45] Date of Patent: Nov. 12, 1985

[54] INSECT REPELLENT: 1-(3-PHENOXY)-PROPYL-2,3-DIBROMO-PROPIONATE

[75] Inventor: Nathan S. Bunker, Pleasant Hill, Calif.

[73] Assignee: Stauffer Chemical Co., Westport, Conn.

[21] Appl. No.: 618,003

[22] Filed: Jun. 6, 1984

[51] Int. Cl.$^4$ .................... A01N 37/12; C07C 69/635
[52] U.S. Cl. .................... 514/550; 514/919; 560/228
[58] Field of Search ........ 560/228; 424/311, DIG. 10

[56] References Cited

U.S. PATENT DOCUMENTS

| | | | |
|---|---|---|---|
| 3,219,688 | 11/1965 | Weil et al. | 560/228 |
| 3,388,150 | 6/1968 | Newallis et al. | 560/228 X |
| 3,711,271 | 1/1973 | Baker | 560/228 X |
| 3,773,824 | 11/1973 | Strong | 560/228 X |
| 3,816,514 | 6/1974 | Siddall | 560/228 X |
| 4,036,984 | 7/1977 | Takahashi et al. | 424/311 |

FOREIGN PATENT DOCUMENTS

| | | | |
|---|---|---|---|
| 0591188 | 1/1960 | Canada | 560/228 |
| 0015817 | 2/1977 | Japan | 424/311 |
| 0008005 | 1/1983 | Japan | 424/311 |

*Primary Examiner*—Natalie Trousof
*Assistant Examiner*—Patricia M. Scott
*Attorney, Agent, or Firm*—Joel G. Ackerman

[57] ABSTRACT

The title compound, 1-(3-phenoxy-propyl-2,3-dibromo-propionate,

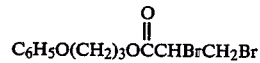

is an insect repellent.

5 Claims, No Drawings

INSECT REPELLENT: 1-(3-PHENOXY)-PROPYL-2,3-DIBROMOPROPIONATE

This invention relates to the novel compound 1-(3-phenoxy)propyl-2,3-dibromopropionate having the formula

$$C_6H_5O(CH_2)_3OCCHBrCH_2Br$$

As will be shown from the data which follows, this compound has been found to have utility as an insect repellent, particularly for repelling flying insects, most particularly, houseflies and mosquitos, from lighting and/or feeding.

The novel compound can be prepared by reaction of 3-phenoxy-1-propanol with a 2,3-dibromopropionyl halide (preferably the chloride) in the presence of a solvent and a base (preferably a tertiary amine) according to the reaction:

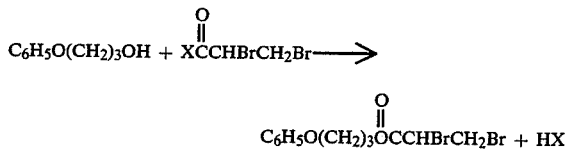

in which X is a halogen.

Solvents suitable for the reaction are those which are inert to the reactants and products. A preferred solvent is methylene chloride. Other suitable solvents are chloroform, benzene, diethyl ether and tetrahydrofuran. The temperature is preferably from about 0° to about 30° C. Suitable bases include tertiary amines such as triethylamine, di(lower alkyl)anilines and pyridine.

The following is an example of the preparation of the subject compound.

In a flask were placed 5.0 grams (g) (0.033 mole) 3-phenoxy-1-propanol, 50 milliliters (ml) methylene chloride and 3.4 g (0.033 mole) triethylamine. The mixture was cooled to 0° C.; then 8.3 g (0.033 mole) of 2,3-dibromopropyl chloride was added (over 5 minutes), the mixture was warmed to room temperature and stirred for 2 hours.

The reaction product mixture was diluted with 50 ml methylene chloride, washed with portions of water, saturated sodium bicarbonate solution and saturated sodium chloride solution, filtered through dry sodium sulfate and dried in vacuo, yielding 10.2 g (85% of theoretical yield) of the desired product, a clear brown oil. The structure was confirmed by infrared, nuclear magnetic resonance and mass spectroscopy.

Insect Repellency Evaluation

Houseflies

The insect utilized for this test was the housefly, *Musca domestica* (L.). One hundred houseflies of mixed sexes were placed in test cages. In each cage was placed a sugar cube saturated with 0.5 or 1.0 ml of acetone containing 0.1 or 1.0% (by weight) of the test compound. Two sizes of sugar cube were utilized—"cocktail" (smaller size) and "normal" (larger size). The cube was dried and weighed before being placed in the cage. Each cage also contained a water-saturated cotton plug to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube treated with only acetone and no test compound, was calculated. The lower the repellency ratio, the greater the repellency of the test compound. The repellency ratios of the test compound at different concentrations are shown in the following Table.

TABLE I

| Test Compound wt. % | Test Solution ml | Sugar Cube | Repellency Ratio |
|---|---|---|---|
| 0.1 | 0.5 | cocktail | 0.95 |
| 0.1 | 1.0 | cocktail | 0.73 |
| 1.0 | 1.0 | normal | 0.17 |

Thus, the test compound was effective as an insect repellent at concentrations as low as 0.1 weight %, with the repellency activity increasing as concentration increased in the acetone solution.

Yellow Fever Mosquito

The insect utilized for these tests was the yellow fever mosquito, *Aedes aegypti*.

Pupae were placed in separate standard fly cages and allowed to emerge into adults. The mosquitos were supplied with a sugar-water solution. Tests were performed at least 3 days after the adults emerged.

The test compound was weighed and dissolved in acetone. One milliliter of the test solution was pipetted onto a 9×9 cm swatch of cotton stocking. The swatches were then allowed to dry for 1 hour.

A square opening 6×6 cm was made in an upper corner of one side of the mosquito cage. A large, hard cardboard disc was placed over the opening so that it could be rotated to either cover or expose the opening as desired. One-half of the disc was left intact. In the remaining half, several 6×6 cm square openings were cut. When the intact half of this disc was located over the opening in the fly cage, this opening was effectively sealed.

Swatches of treated stocking were placed over the square holes in the disc and held in place by metal frames attached to magnetic tape.

To initiate the test, the disc was rotated so that a treated swatch became located over the opening in the cage. The palm of the tester's hand was placed over a cardboard ring 8 cm in diameter and 1 cm thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing through the cloth was recorded during a 1-minute exposure. Repellency was considered to occur when 5 or fewer insects probed the swatch during the exposure.

The compound was tested at application rates of 1 ml of 0.1% solution per swatch or 0.0123 mg/cm². The results of these tests are contained in Table II.

TABLE II

| Test No. | Insects probing, 1 min. |
|---|---|
| 1 | 9 |
| 2 | 3 |
| 3 | >10* |

*Residual testing - 3 days after impregnation.

The novel compound of this invention may be used as an insect repellent in either diluted or undiluted form. When used in a diluted form, compositions may contain relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface-active agents, anti-oxidants and propellants which may be normally found in insect repellent preparations. The active compound of this invention may be employed as the sole active component of such compositions or may be used in admixture with other compounds having a similar or different utility. For example, the compound may be incorporated into creams, lotions, powders, suntan oil, insecticides and other preparations which may contain pesticidal or other useful substances, as well as into compositions of various types used for treating fabrics or articles of clothing to render them insect repellent. In general, compositions for repellent use may contain from 0.1 up to 95 weight %, preferably from 1 to about 40 weight %, of the novel compound. High concentration formulations, containing up to 95% of the compound, could also be utilized for low-volume spraying from the air.

Examples of typical formulations employing the compound of this invention are for instance,

EXAMPLE 1

Emulsifiable Concentrate

| Component | Weight % |
|---|---|
| Active Compound | 53.6 |
| Aromatic Hydrocarbon Solvent | 36.4 |
| Emulsifier | 10.0 |
| Total | 100.0 |

EXAMPLE 2

Lotion

| Component | Weight % |
|---|---|
| Active Compound | 10.7 |
| Lanolin | 4.8 |
| Mineral Oil | 8.0 |
| Trihydroxyethylamine stearate | 1.8 |
| Glycosterin | 0.8 |
| Glycerine | 4.6 |
| Sodium Benzoate | 1.0 |
| Water | 68.3 |
| Total | 100.0 |

EXAMPLE 3

Alcohol Solution

| Component | Weight % |
|---|---|
| Active Compound | 53.6 |
| Isopropanol | 46.4 |
| Total | 100.0 |

EXAMPLE 4

Alcohol Solution

| Component | Weight % |
|---|---|
| Active Compound | 80.0 |
| Ethanol | 20.0 |
| Total | 100.0 |

EXAMPLE 5

Wettable Powder

| Component | Weight % |
|---|---|
| Active Compound | 26.9 |
| Hydrated Calcium Silicate | 62.1 |
| Sodium Lignosulfonate | 5.0 |
| Orzan A (mixture of ammonium lignosulfonate and wood sugars) | 5.0 |
| Wetting Agent | 1.0 |
| Total | 100.0 |

What is claimed is:

1. A compound having the formula

wherein $C_6H_5$ is phenyl.

2. An insect repelling composition containing an amount of a compound having the formula

wherein $C_6H_5$ is phenyl, effective to repel insects from lighting or feeding and an inert diluent or carrier suitable for insect repellent compositions.

3. A method for repelling insects comprising applying to a locus to be protected from insects, an amount of a compound having the formula

wherein $C_6H_5$ is phenyl, effective to repel insects from said locus.

4. A method according to claim 3 in which the insect is the housefly.

5. A method according to claim 3 in which the insect is the yellow fever mosquito.

* * * * *